United States Patent [19]
Adair

[11] 3,946,741
[45] Mar. 30, 1976

[54] URETHRAL CATHETER AND BODY DRAINAGE DEVICE

[76] Inventor: Edwin L. Adair, 3535 S. Lafayette, Englewood, Colo. 80110

[22] Filed: Dec. 9, 1974

[21] Appl. No.: 530,840

[52] U.S. Cl.............................. 128/347; 128/349 R
[51] Int. Cl.²......................................... A61B 17/34
[58] Field of Search........................ 128/347–351, 128/243, 244, 242, 241; 27/24

[56] References Cited
UNITED STATES PATENTS

| 318,535 | 5/1885 | Bihler | 128/243 |
| 1,719,428 | 7/1929 | Friedman | 128/242 |
| 1,733,189 | 10/1929 | Friedman | 128/242 |
| 1,870,942 | 8/1932 | Beatty | 128/241 |
| 3,108,595 | 10/1963 | Overment | 128/350 |

*Primary Examiner*—Lawrence W. Trapp
*Attorney, Agent, or Firm*—Sheridan, Ross & Fields

[57] ABSTRACT

Catheter of the telescope tube, expandable wing type, characterized by the provision of alternative forms of means for preventing outward leakage from between the tubes, the leakage preventing means also serving the additional purpose of retaining the wings in expanded position. Alternative forms of tube distal ends are disclosed including one form for removing clots from blood vessels. Also, a stiff trochar rod may be employed with various forms of seals and the tube distal ends.

9 Claims, 6 Drawing Figures

U.S. Patent  March 30, 1976  3,946,741
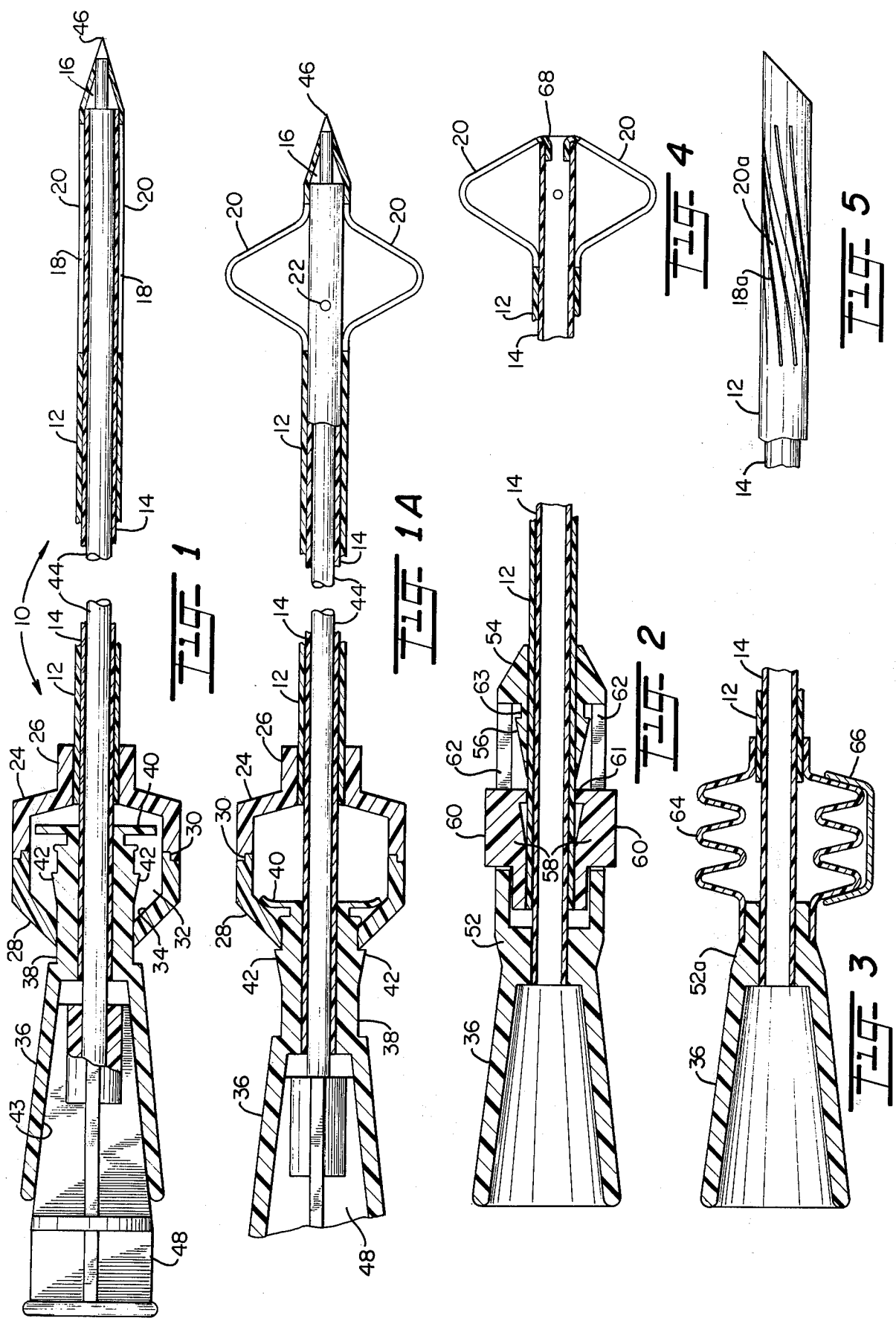

URETHRAL CATHETER AND BODY DRAINAGE DEVICE

BACKGROUND OF THE INVENTION

Telescopic tube catheters of expandable wing type are well known, exemplary of which is that disclosed in U.S. Pat. No. 3,108,595 to Overment. In such type, the distal ends of the tubes are secured together, longitudinal angularly spaced slits are provided in the outer tube adjacent its distal end so that when the tubes are slid relatively, the wings formed between the slits are expanded to prevent unauthorized removal from a body passage. Suitable means are also provided to lock the wings in expanded position. Since the tubes are normally provided with some clearance therebetween to render them readily slideable, fluids may leak through the clearance to the outside of the catheter which is objectionable for obvious reasons.

SUMMARY OF THE INVENTION

The present invention relates to a catheter of the type just referred to but adds alternative forms of sealing devices for preventing leakage from between the tubes. The sealing means also provides a lock for retaining the wings in expanded position. In one form, a chamber is secured to the proximate end of the outer chamber which chamber is sealed at its other end by a flange secured to the inner tube. In another form, the outer tube is squeezed onto and in sealing engagement with the inner tube. In still another form a resilient bellows is provided, one end of which is secured to the outer tube and the other to the inner tube, forming a chamber which may trap any leakage from between the tubes. One form of means for securing distal ends of the tubes together permits the wings to be disposed closer to the distal ends, reducing the projection of the distal ends into a body cavity or the like. Another form of outer tube provides helical wings which are adapted to remove clots from blood vessels rather than to form locking means for retaining the tubes in a fixed position.

In accordance with the foregoing, one of the principal objects of the invention is to provide various combined fluid seals and wing locks for telescopic tube catheters.

Another object is to provide a trochar which may be employed with catheters of the type, aforesaid.

A further object is to provide improved distal ends for slideable tube catheters and the like.

Still further objects, advantages, and salient features will become more apparent from the detailed description to follow, the appended claims, and the accompanying drawing to now be described.

BRIEF DESCRIPTION OF THE DRAWINGS

FIG. 1 is a central longitudinal section through one form of the invention;

FIG. 1A is a like section illustrating a different position of the parts;

FIG. 2 is a like section through an alternative form of seal;

FIG. 3 is a like section through another alternative form of seal;

FIG. 4 is a like section through an alternative form of tube distal ends and expandable wings; and FIG. 5 is a like section through another alternative form of tube distal ends and expandable wings.

DESCRIPTION OF PREFERRED EMBODIMENT

Referring now to the drawing, and first to FIG. 1, catheter 10 comprises an outer plastic tube 12, an inner slideable plastic tube 14, the distal ends being secured together by a heat seal 16. The outer tube is provided with a plurality of equiangularly spaced slits 18, such as four, which provide expandable wings 20 when the tubes are moved relatively, the expanded position being shown in FIG. 1A. An aperture 22 is also provided in inner tube 12 which provides communication from the left or proximate end thereof and a body organ or the like, the wings permitting insertion of the catheter through a body passage when they are collapsed and preventing removal when they are expanded, usually adjacent the distal end of the body opening, the construction as so far described, being essentially the same as in the overment patent, previously referred to. Also, the clearance between the tubes is such that fluid may flow therethrough but differs in that any flow or leakage is prevented from flowing to the exterior of the catheter, the means for preventing such leakage to now be described.

A circular plastic cup shaped member 24, having a collar or boss 26, is secured to outer tube 12 in any suitable manner, such as by a heat seal or cement, and a similar cup shaped member 28 is similarly secured to cup member 24 at a joint 30. As will be apparent, the two cup members form a cylindrical chamber 32 having a frusto-conical wall 34 at one end thereof.

A conduit fitting 36, having a circular hub 38, is secured to inner tube 14, the hub being slideable within a circular aperture in wall 34. The right or distal end of the hub is provided with a flexible circular flange 40 and a pair of oppositely disposed detents 42 are provided at spaced points from the flange. When member 36 is moved from the position of FIG. 1 to that of FIG. 1A, detents 42 pass through the aperture in wall 34 and lock against its outer edge. At this position, flange 40 engages the frusto-conical wall 34 in flexed condition, preventing leakage around its outer edge. As will be apparent, the detents also lock wings 18 in expanded position, all as best shown in FIG. 1A. The left or proximate end of member 36 is formed with a frusto-conical wall 43 into which a male fitting may be inserted, the fitting being connected to a hose for delivering fluid to inner tube 14 or draining fluid therefrom. My U.S. Pat. No. 3,692,029 discloses an exemplary fitting of such type.

The catheter of FIGS. 1 and 1A, as so far described, may be used in the normal manner for application through a curved or tortuous body passage since the telescopic tubes are sufficiently flexible to conform to the curvature of the passage. In some instances, however, a stiff catheter is desired for insertion through a portion of the body, such as through the body chest. To attain this a trochar rod 44 formed of metal, such as stainless steel, may be inserted into inner tube 14, the rod having a sharp conical point 46 at its distal end which extends slightly beyond the distal ends of tubes 14, 12 and provided at its proximate end with a frusto-conical finger engaging member 48 which seats within frustoconical female fitting 36. After applying the catheter and its trochar into desired position the trochar is removed, and the wings are moved to expanded position, as previously described.

Referring now to FIG. 2, this illustrates an alternative form of seal. It comprises a member 52 affixed to the inner tube 14 having a portion 54 which slideable receives outer tube 12 and including a conical portion 56 which may be contracted onto the outer tube. The means for contracting same comprises an annular collar 58 affixed to the outer tube, and having knobs 60 extending through angularly spaced slots 62. When the two tubes are moved relatively by outward relative movement of member 52 and knobs 60, collar 58 moves onto conical portion 56 contracting it and the outer tube onto the inner tube, providing a seal therebetween. Detent 61, which may be in the form of a flange, then locks in groove 63, locking the wings in expanded positions.

Referring now to FIG. 3, this illustrates another alternative form of seal. This comprises a member 52a secured to inner tube 14, as in FIG. 2, and a bellows 64, one end of which is secured to member 52a and the other to outer tube 12. The bellows is preferably resilient and disposed in its expanded position (not shown) with wings 20 disposed in their expanded positions. When it is desired to collapse the wings, the tubes are slid relatively to the position shown, collapsing the bellows. The bellows are retained in the collapsed position, as shown, by any suitable locking means or keeper 66. After inserting the tubes into a body passage, the lock or keeper 66 is removed and the resilience of the bellows moves the wings to their expanded positions. As will be apparent, this seal differs somewhat from the others disclosed in that leakage from between tubes 12, 14 is prevented at all times whereas in the others leakage is prevented only when the wings are moved to their expanded positions. The latter, however, is of no disadvantage since leakage is a problem only when in use, that is, when the wings are expanded.

Referring now to FIG. 4, this illustrates an alternative manner of securing the distal ends of the tubes together. Outer tube 12 is provided with a fold or retroverted end 68 which is heat sealed to the end of inner tube 14. This construction permits slits 18 and wings 20 to be disposed somewhat closer to the ends of tubes 12, 14 so that there is a reduced projection of the catheter beyond the wings.

Referring now to FIG. 5, this illustrates another form of wing construction. It comprises a plurality of helical slits 18a, such as six, which provide a plurality of wings 20a. Also, the distal ends of the tubes terminate at an angle to their axes, as illustrated. The principal utility of the helical wings is in removing blood clots from blood vessels. In use, it is inserted into the vessel through and beyond the clot and then expanded to a size to engage the wall of the vessel. It is then removed, usually with the aid of suction in the inner tube, forcing the clot ahead of the wings. The helix angle and length of helix should preferably be such that the expanded wings provide a plug ahead of the clot to obviate leakage between ends of the wings which could occur if the expanded wings were disposed parallel to the outer tube as in the other figures.

In addition to the various constructions disclosed herein to prevent leakage between the inner and outer tubes an O-ring may be used between the tubes.

As will be apparent, the various seals disclosed, the various tube distal ends, and the trochar rod may be employed in numerous combinations within the purview of the invention, the illustrations thus being exemplary and in the interest of simplifying the disclosure.

What is claimed is:

1. In an instrument of the type having inner and outer relatively slideable telescopic tubes having distal ends secured together and having wings on the outer tube adjacent its distal end adapted to expand upon relative axial movement of the tubes, said tubes adapted to be disposed within the human body with their distal ends at a desired position therewithin and their proximate ends outside of the body, the tubes being subject to fluid leakage therebetween to outside of the instrument at the proximate end of the outer tube, the improvements, in combination, comprising:
   a. sealing means disposed adjacent the proximate end of the outer tube for preventing said outward leakage, at least when the wings are in expanded position,
   b. said means being so constructed to also lock the wings in expanded position.

2. An instrument in accordance with claim 1 wherein said means comprises a closed chamber having one end secured to the distal end of the outer tube, its other end having a wall with a central aperture therein, a member affixed to the proximate end of the inner tube and slideable within said aperture, said member having a flange thereon adapted to sealingly engage said wall within said chamber, and means for locking said flange in sealing engagement with said wall.

3. An instrument in accordance with claim 1 wherein said means comprises a member affixed to the proximate end of the inner tube and having a conical portion in which the outer tube may slide, and means affixed to the outer tube adapted to engage said conical portion and contract the outer tube into sealing engagement with the inner tube, the last named means, when in the position aforesaid, adapted to lock the tubes against relative axial movement with the wings in expanded position.

4. An instrument in accordance with claim 1 wherein said means is so constructed to prevent leakage in all positions of relative axial movement of the tubes.

5. An instrument in accordance with claim 4 wherein said means comprises a bellows having ends secured to the two tubes.

6. An instrument in accordance with claim 5 wherein the bellows is resiliently urged toward wing expanded position.

7. An instrument in accordance with claim 6 including means for retaining the bellows in collapsed position with the wings also in collapsed position.

8. An instrument in accordance with claim 1 wherein said means is provided with a frusto-conical bore adapted to receive a like shaped fluid communicating fitting.

9. An instrument in accordance with claim 1 including a stiff metallic trochar rod extending through the inner tube, said rod having a pointed distal end disposed beyond the distal ends of said tubes adapted to facilitate entry of the tubes into the body, its proximate end being accessible for removing same from the inner tube after the two tubes have been disposed in desired position in the body.

* * * * *